United States Patent [19]

Maher et al.

[11] Patent Number: 4,832,033
[45] Date of Patent: May 23, 1989

[54] ELECTRICAL STIMULATION OF MUSCLE

[75] Inventors: Daniel V. Maher, Greenwich, Conn.; Conor Minogue, Ballybeg, Ireland

[73] Assignee: Bio-Medical Research Limited, Clare, Ireland

[21] Appl. No.: 856,235

[22] Filed: Apr. 28, 1986

[30] Foreign Application Priority Data

Apr. 29, 1985 [GB] United Kingdom ................. 8510832

[51] Int. Cl.⁴ ............................................... A61N 1/36
[52] U.S. Cl. ................................. 128/421; 364/413.27
[58] Field of Search ............... 128/419 R, 420 R, 421, 128/422, 423 R, 419 PT, 419 PG; 364/413

[56] References Cited

U.S. PATENT DOCUMENTS

| | | | |
|---|---|---|---|
| 4,232,679 | 11/1980 | Schulman | 128/419 PG |
| 4,361,153 | 11/1982 | Slocum et al. | 128/419 PT X |
| 4,365,633 | 12/1982 | Loughman et al. | 128/419 PG |
| 4,485,818 | 12/1984 | Leckrone et al. | 128/419 PG |
| 4,502,275 | 3/1985 | Chen . | |
| 4,503,863 | 3/1985 | Katims | 128/421 X |
| 4,541,432 | 9/1985 | Negro | 128/421 |
| 4,690,144 | 9/1987 | Rise et al. | 128/419 R |

FOREIGN PATENT DOCUMENTS

| | | | |
|---|---|---|---|
| 1175493 | 10/1984 | Canada | 128/421 |
| 0165049 | 12/1985 | European Pat. Off. . | |
| 3207050 | 2/1982 | Fed. Rep. of Germany . | |

Primary Examiner—Lee S. Cohen
Attorney, Agent, or Firm—Fleit, Jacobson, Cohn & Price

[57] ABSTRACT

A muscle stimulation system which stimulates muscles with electrical pulses supplied to electrodes applied to the skin overlying the muscle comprises a system controller and one or more personally portable stimulator units, each provided with electrodes. The system controller stores data relating to the characteristics of pulses to be applied to the muscle e.g. Trophic or functional or a combination thereof, and is adapted to download this data to a personal stimulator unit either by an infra-red link or by programming a programmable memory module which is then connected into the stimulator unit. The electrodes are applied to the skin of the patient and supplied with the pulses programmed into the stimulator unit, the stimulator unit being carried by the patient. The system controller may be adapted to be controlled by a personal computer and may also be provided with its own muscle stimulator.

13 Claims, 5 Drawing Sheets

ELECTRICAL STIMULATION OF MUSCLE

The present invention relates to muscle stimulators and to the communication of stimulation data between a muscle stimulator and another device.

Muscle stimulators are known which provide for the electrical stimulation of muscles by application of pulses to an electrode arrangement applied to the skin overlying the muscle. In the prior art, a certain amount of adjustment of the characteristics of the pulse train has been possible by the operator. The present invention is, in part, concerned with providing an arrangement whereby the characteristics of a pulse series may be adjusted.

The present invention encompasses several different concepts which may be used either singly or in any desired combination with one another.

According to the present invention there is provided a muscle stimulator system comprising (a) at least one muscle stimulator apparatus, for the electrical stimulation of muscles by the application of electrical pulses to an electrode arrangement applied to the skin overlying the muscle, (b) a system controller having means defining stimulating characteristics of electrical signals and means for transferring from the system controller to the or each stimulator apparatus data defining the characteristics of the electrical pulses, the stimulator apparatus being adpated to be operable remote from the system controller. The stimulator and remote device are preferably so adapted that data can be transferred between them without a direct electrical connection between them such as, for example, by means of an optical data link, an ultrasonic link, a radio link, etc. Data may instead or as well be transferred between them via a communication network, for example via a telephone network using modems or acoustic couplers.

One of the reasons why it is desirable to provide for a transfer or data to enable the stimulation pulse characteristics to be changed is that although in the past the stimulation applied to the muscles has been essentially functional stimulation, i.e. simply causing a predetermined contract/relax cycle of the muscles, recently a new technique, known as "trophic" stimulation has been developed which, by suitable choice of the characteristics of the stimulation pulse series, can bring about a long term functional and/or structural change in the fibres of the muscle being stimulated. This is currently being developed with a view to providing therapeutic treatments for muscular disorders and dysfunctions and the particular trophic stimulation required for a particular muscle will vary. It is contemplated that the remote device will have access to a database of trophic code pulse series characteristics from which the appropriate data can be down loaded to the stimulator for application to the muscle in question. It is also contemplated that certain treatment regimes will require a combination of function and trophic stimulation with periods of trophic stimulation being interspersed with periods of functional stimulation. The data down loaded may thus comprise both functional and trophic stimulation data as well as data relating to how the two various patterns of stimulation are to be applied in sequence.

The stimulator apparatus may preferably be of a shape and size such as to be personally portable, preferably carried about the person e.g. pocketable. Thus one embodiment of this aspect of the present invention contemplates the provision of a stimulator of approximately the same size and possibly shape as the personal cassette players which have recently come on to the market and, as with such players, the stimulator may be housed in a casing which is adapted, for example by the provision of a clip, belt loop, carrying strap or other attachment means to facilitate the stimulator being carried or worn about the person.

It will be appreciated from the above that the present invention allows "out patient" treatment of a patient at home, with the patient being provided with a personal muscle stimulator which is adapted so that it can be readily be carried around by him or her and which can be programmed by a trained operator from a clinic either by taking the stimulator to the clinic for reprogramming or by transmitting data to it e.g. over the telephone link.

The personal stimulator, whose operation may be controlled by a suitably programmed microprocessor, can be arranged to record in a memory the history of use of the stimulator since the last updating of the pulse series data so that, for example, this information can be transferred back to the remote device to give an indication of how much the stimulator has been used so that the appropriate next set of stimulation data to continue a particular course of treatment can be down-loaded.

The muscle stimulator system controller may also include a muscle stimulator, as well as circuitry for enabling data defining a stimulation pulse series to be transferred to a remote muscle stimulator such as the personal stimulator mentioned above. This allows the system controller to be used as a stimulator in its own right and to control and manage stimulation provided by one or more remote stimulators. Thus one application of this controller which is currently contemplated is that a clinician would have the system controller for his or her use in treatment and/or research, with the facility being provided to down-load data to individual personal stimulators carried by patients or research subjects. The system controller may also have an interface to enable it to exchange data with a computer database held, for example, on a personal computer. Thus the clinician could build up or access a database of stimulation pulse data from which appropriate data could be selected for a particular treatment and then downloaded to a suitable personal muscle stimulator.

For this purpose, it is contemplated that the muscle stimulator section of the system controller will provide a reasonably comprehensive set of controls for enabling the pulse characteristics of a pulse train to be determined, i.e. pulse repetition rate, interval, length, amplitude and so forth. A number of parallel output channels with independent amplitude controls may be provided.

Preferably the system controller may be used in association with a muscle stimulation control device which is provided with circuitry which interacts with the circuitry of the system controller so as to place the functions and controls of the system controller under the control of a separate computer, e.g. a personal computer, so that the system controller can be operated by the keyboard (or other input device) of this computer.

Conveniently the system controller may also be fitted with a printer by which the operator can generate for instance a summary of an individual patients treatment regime, data relating to the measured electrode impedance.

Preferably the stimulation pulse data is transferred in the form of predetermined binary words, e.g. ASCII characters used to represent particular parameters, and parameters values, of a stimulation pulse series. The details of one such coding arrangement will be described below.

The stimulator may further be provided with a radio receiver, and the system controller with a radio transmitter, the stimulator outputting the electrical pulses in response to trigger signals transmitted from the system controller. Alternatively the stimulator may be provided with a timer to generate trigger signals which cause electrical pulses to be supplied to the electrodes.

The invention will be further described by way of example with reference to the accompanying drawings in which.

Figure 1A:
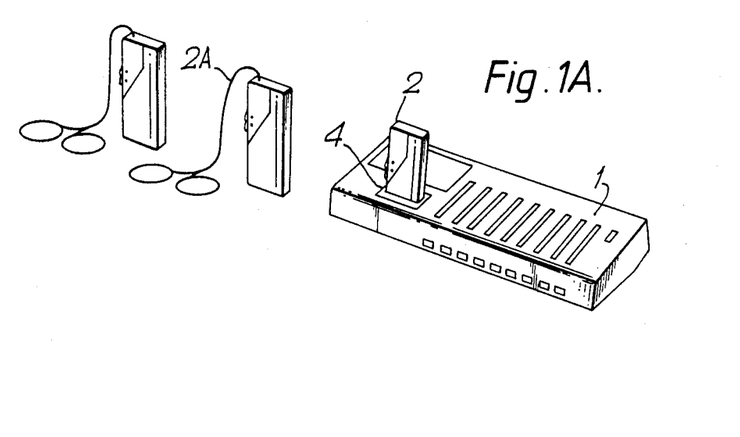
FIGS. 1a, 1b and 1c show the individual units of one embodiment of system according to the present invention in three different operating configurations.
Figure 1B:
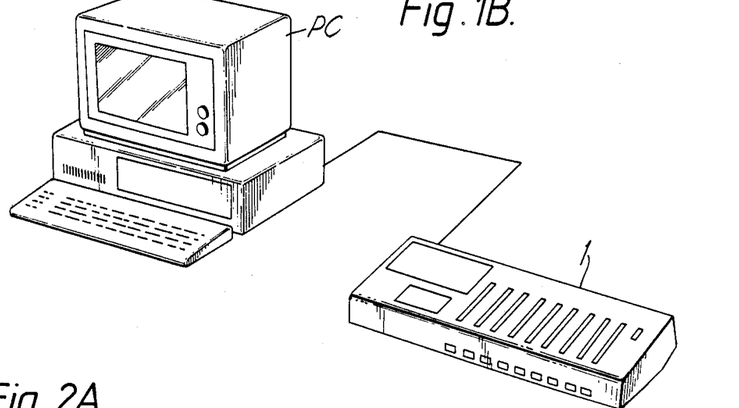
Figure 1C:
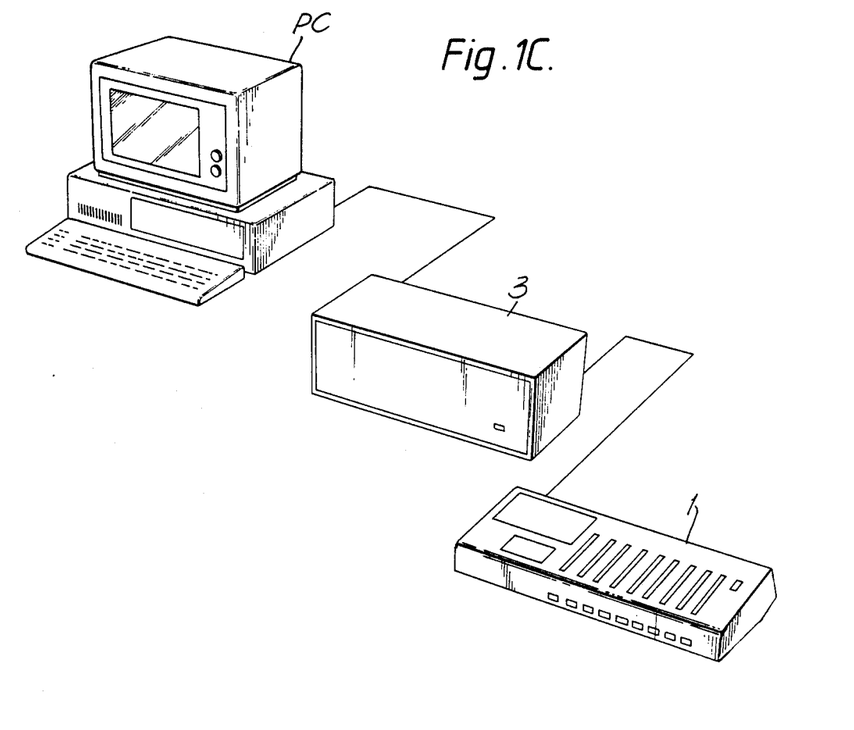

FIGS. 1a, b and c show the three principal components of a system according to the present invention in three different operating configurations. These components are:

A system control unit 1. This is an 8-channel, programmable muscle stimulator unit with additional facilities for interfacing the unit with the other unit of the system and also with computers such as the personal computer PC shown in FIG. 1b;

One or more personal stimulators units 2 which are preferably of a shape size and weight enabling them to be personally portable, preferably pocketable. The stimulation pulses produced by this unit may be changed as desired and conveniently may be so changed by reprogramming by the system unit 1 as shown in FIG. 1a.

A "research" unit 3, shown in FIG. 1c, and so called because it is intended, at least initially to facilitate research and development on muscle stimulation and to enable courses of treatment involving a regime of stimulation patterns to be evolved.

Referring first to FIG. 1a, the personal unit 2 is conveniently similar in shape and size to the personal cassette players which have recently become available and has associated with it one or more pairs of electrodes 2i a by means of which the stimulating pulses can be applied to the skin overlying the muscle to be stimulated. This pair of electrodes may plug into the stimulator for use and be stored in with a carrying pouch for when not in use.

Figure 2A:
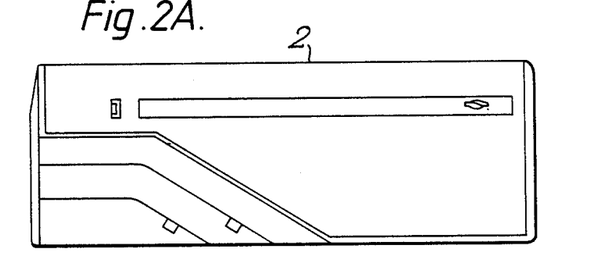
FIGS. 2a, 2b and 2c are views showing a personal stimulator unit in the embodiment of FIG. 1.
Figure 2B:
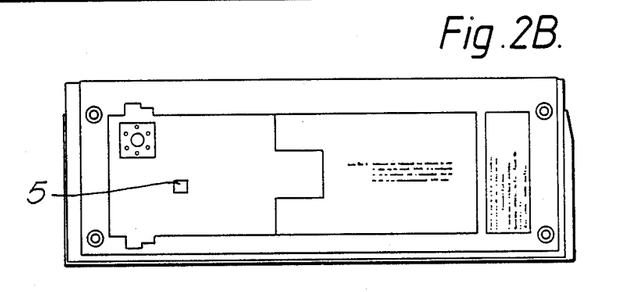
Figure 2C:
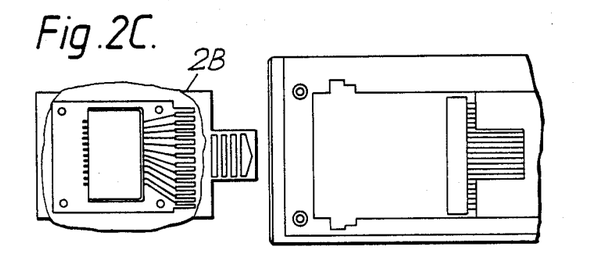

The characteristics of the stimulation pulses, such as their length, interval between them, modulation into bursts and so forth are controllable by its internal circuitry in accordance with a stored programme. This programme may be placed in the unit in any one of a number of ways, for example by having a replaceable memory module (such as 2B shown in FIG. 2c) which fits into the unit but instead of or in addition to this, the unit preferably has a specially adapted interface arrangment whereby the desired pulse stimulation pattern(s) can be down-loaded to the unit from the system controller 1.

Conveniently the above mentioned down-loading of the stimulation pulse characteristics is achieved by means of a physical and electronic interface which does not involve direct electrical connection between the unit 2 and the system controller 1. It will be apparent that any one of a number of means could be used to achieve this, for example an optical (including infra-red) link, an ultrasonic link or magnetic induction link, the optical/infra-red link currently being preferred. For this purpose, the top, sloping panel of the system controller 4 is provided with a receptacle 4 in which a unit 2 may be stood. Inside the receptacle is an infra-red transducer which is directly aligned with an infra-red transducer 5 on the back surface of the unit 2. Whatever form the link takes, it is preferred that it allows for data transfers in both directions between the unit 2 and the controller 1. In addition to the principal intention of down-loading data to the unit 2, this is partly to facilitate establishing a communication protocol between them (e.g. to handle transmit and break transmit requests and so forth) and partly to enable the unit 2 to transfer information back to the system controller 1 for purposes to be described below.

Figure 3:
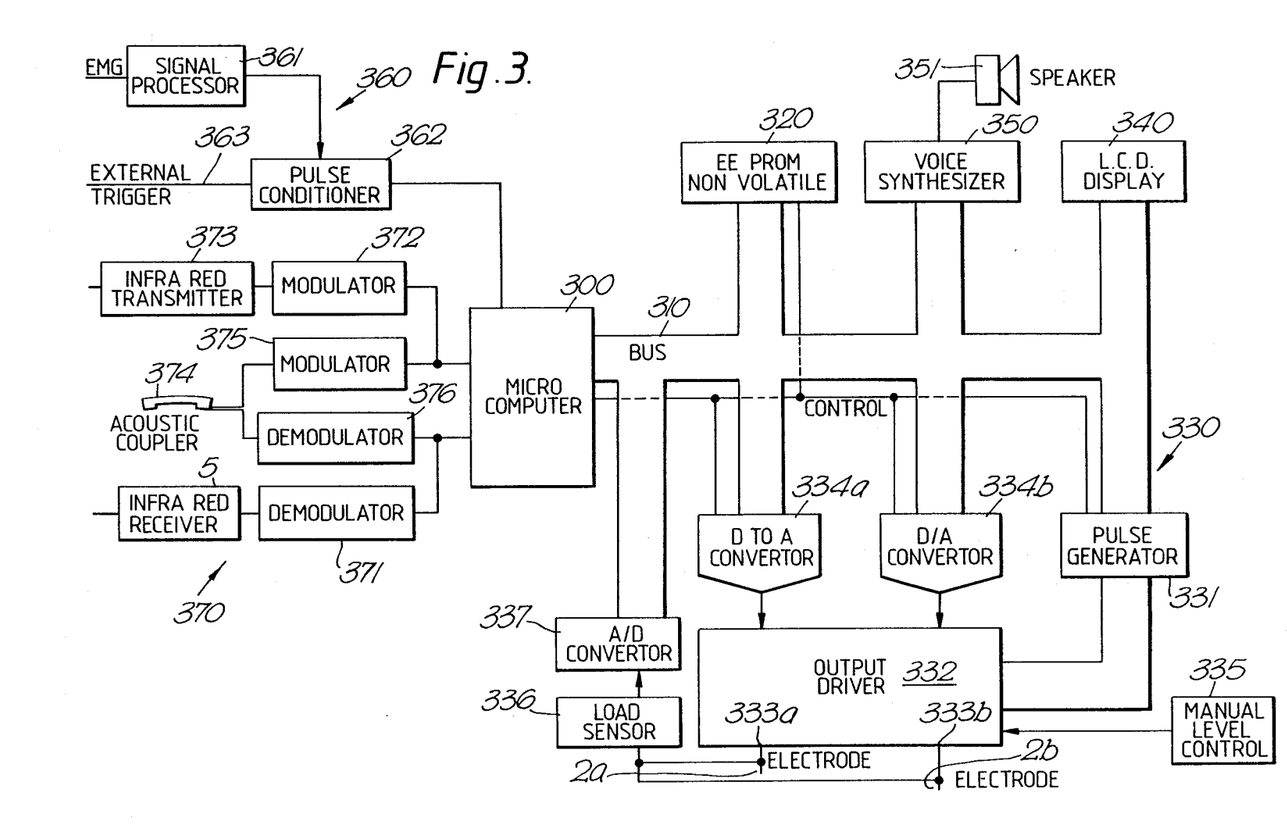
FIG. 3 is a block diagram of the circuitry in the personal stimulator unit of FIG. 2.

The internal circuitry of the unit 2 is shown in block form in FIG. 3. It comprises a microcomputer 300 which may be implemented by means of a microprocessor and controls and co-ordinate the operation of the other parts of the circuitry. Connected to the microcomputer 300 via a data bus 310 is a memory 320 in which data can be stored defining the desired characteristics of the stimulating pulses. This memory may be wholly read-only, part read/write and part read-only or wholly read/write (note that this is referring to memory in which the stimulating pulse data is stored; such memory is required for operation of the microprocessor, if such is used as the microcomputer 300 may be provided separately, if desired and be, for example mask programmed). In the present case, where it is intended that the data is down-loaded from the system controller 1 to the unit 2, at least part of the memory 320 will require to be read/write memory and preferably, also, non-volatile so that the unit can be used remotely from the system controller 1, without requiring reprogramming between uses. For this purpose the memory 320 may be the nature such that it is inherently non-volatile, such as magnetic bubble memory or, for example, a low consumption CMOS memory with battery back-up or electrically alterable memory the latter being preferred.

Reading and writing operations to and from the memory 320 are carried out by the microcomputer 300 which carries out the function of loading the data into the memory and outputting it to a programmable pulse generator 330 which, in response to the data read out from the memory 320 generates a train of pulses as defined by the data, this in turn being connectd to an output interface which drives the electrodes 2a.

It will be seen that the programmable pulse generator is connected to the microcomputer 300 and memory 320 by means of the data bus 310. Also connected to the bus are an LCD display 340 and a voice synthesizer 350 which drives a loudspeaker 351.

The programmable pulse generator 330 comprises a pulse generator 331 which converts data on bus 310 to pulse characteristics and delivers the pulses so formed to output drive circuitry 332 which can provide two channels 333a and 333b of output signals for the electrodes 2. Two digital to analog converters 334a and 334b are provided, by means of which the envelope of the pulse train delivered from the pulse generator 331 may be modulated to provide a particular envelope waveform at the associated outputs 333.

There are also provided a manual level control 335 for the outputs to the electrodes and, a load sensing circuit 336 and analog to digital converter 337 which sense the loading on the electrodes connected to the output 333a and 333b and feed this information back in digital form to the microcomputer 300 via the data bus 310.

The device may thus be arranged to be responsive to changes in the patient's skin resistance. By this or other means [e.g. separate electrodes applied to the skin] it may also be possible to feed back information relating to muscle firming so as to optimise the manner of pulse generation vis-a-vis the intended purpose of stimulation.

Thus the stimulus signal may be altered dynamically depending on the muscle response.

The microcomputer may be programmed to be responsive from electromyographic signals from the patient by means of an electromyographic section 360 comprising a signal processor 361 and pulse conditioning circuit 362. This pulse conditioner 361 may also respond to an external trigger applied to an input 363.

The LCD display 340 and the voice synthesizer 350 may be used by suitable programming of the microcomputer 300 to output information such as instructions on the use of the stimulator, usage data and so forth to the user, programmer or patient.

Data, in particular defining the characteristics of the stimulating pulses which are to be generated, may be loaded into the memory from the system controller or other remote host via a data transfer section 370. This includes the infra-red detector 5 and a demodulator/serial-to-parallel converter 371. A complementary arrangement of a modulator 372 and an infra-red transmitter 373 are provided so that data, e.g. statistical data relating to stimulation applied via the electrode 2 may be returned to the system controller or host. Data may also be passed to and from the system controller or a remote host via the telephone lines e.g. by means of an acoustic coupler 374 (this being preferable from the portability point of view to a hard-wired modem) with associated modulator 375 and demodulator 376.

Any suitable modulation scheme e.g. frequency shift keying may be used for both the infra-red and acoustic links.

Figure 4:
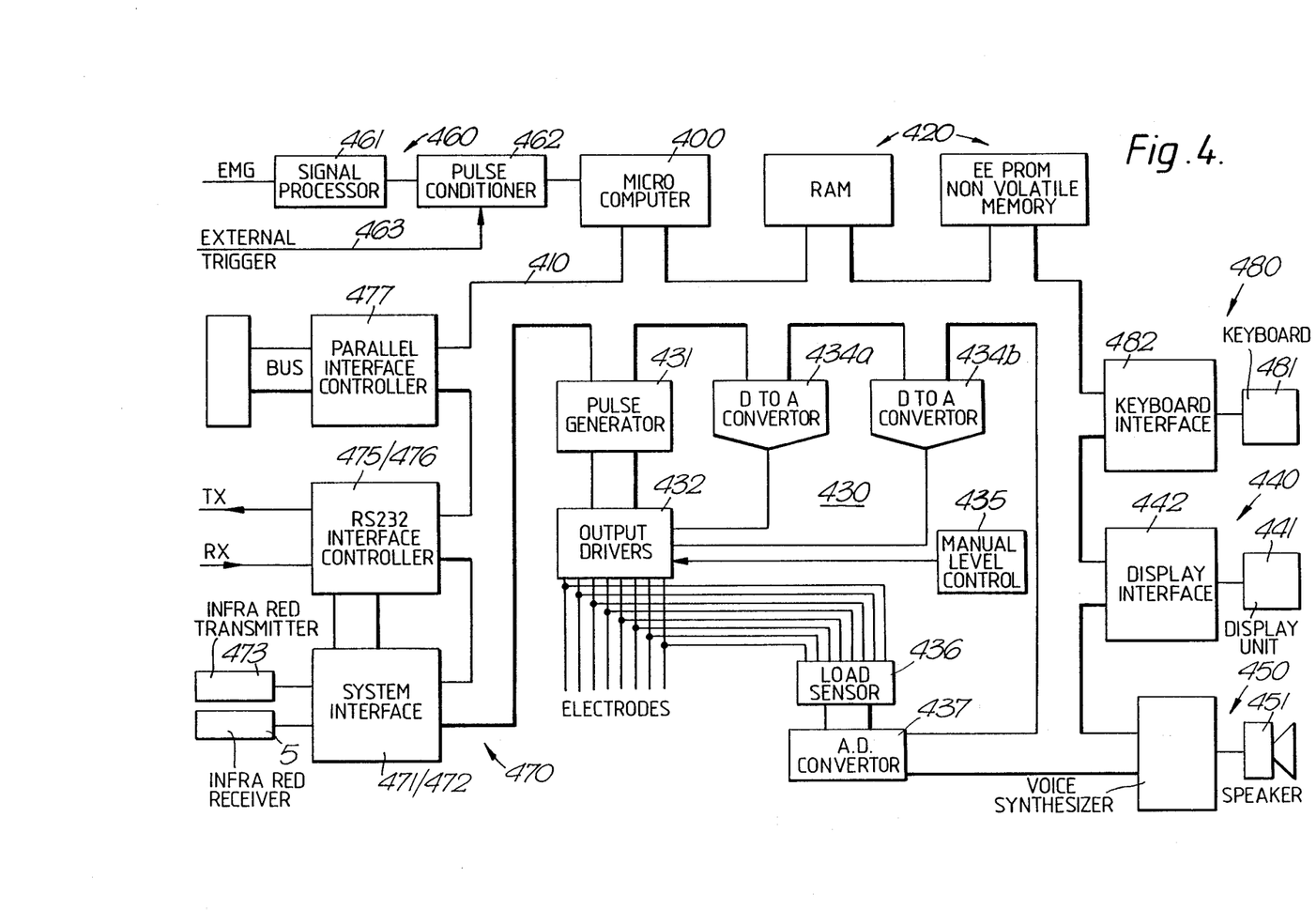
FIG. 4 is a block diagram of the system controller unit of FIG. 1.

FIG. 4 shows in block diagram form the system control unit 1 of the system. It willbe seen that it is generally similar to the circuitry of FIG. 3 but with extra and more flexible features. Those elements that perform functions equivalent to counterparts in FIG. 3 have counterpart reference numerals but with the leading "3" changed to "4".

As in the personal unit, with the system controller has timing control circuitry 400 which, as with the personal unit 2, may be a specially-programmed microprocessor, a memory 420 for programme and data storage, a programmable stimulation pulse generator 430 and a data transfer section 470 exchanging data between the memory 420 and other devices.

The control unit is also provided with a number of user-operable controls 480, suitably provided by keyboard 481 and keyboard interface 482 to programme the microcomputer 400 and to preset the characteristics of the pulse trains to be generated by each channel of the programmable generator 430. These characteristics may include the intervals pulses, the lengths of the pulses, the mean repetition rate of the pulses, envelope modulation of the pulses into bursts. Various other controls may be provided to control the operation of the unit and to provide, for example, that the characteristics of a particular pulse stimulation pattern, once established, can be stored in the system controller 1 and later be retrieved to set the programmable pulse generator 430. This generator, in this example, has 8 parallel output channels, all fed with the same pulse train (although the generator may provide for separate pulse trains for each channel) and may have an independent level control for each channel. These level controls may be digitally controllable.

The microcomputer 400 may be suitably programmed so as to be responsive to user input from the keyboard 45 to carry out a number of tasks, including:

1. The definition/setting up of the characteristics of stimulating pulse sequences, these characteristics being stored in the microcomputer memory 420 and, according to the user's requirements either used to generate a stimulating pulse train by the pulse generator 430 or to be transferred via the data transfer section 470 to a remote device such as a remote host or one of the personal units 2, to a remote or to a data file in a mass storage unit such as disc drive (not shown).

2. To initiate the storage/retrieval of data to/from a remote host via the section 470, or to the personal unit 2 or a data file in a mass storage unit.

3. To instruct the microcomputer 400 to display on display 441 pulse stimulation train data or treatment data, file directories and so forth.

It will be seen that the pulse generator 430 of the system controller is of similar structure to the pulse generator 330 of FIG. 3 and is intended to operate in a similar manner. It has a pulse generator 431 which takes digital data from the data bus 410 and converts this to stimulating pulses which are distributed to the eight output channels by means of the output driving circuitry 432. The load sensor 436 is adapted to take information from each of the eight output channels rather than the two output channels of FIG. 3.

The system controller 1 also includes an EMG responsive section 460 corresponding to that of FIG. 3 and a voice synthesizer and associated loudspeaker 450 corresponding to that of FIG. 3.

It will be seen that the data transfer section includes a parallel interface 477 for rapid, parallel transfer or data to and from e.g. a computer, a mass storage device such as a disc- or tape-store, or any other appropriate data logging, storage or processing system.

The stimulation pulse trains which are produced by the personal unit 2 and by the unit 1 (in the latter case, whether for immediate use using the programmable pulse generator 430 or to be down-loaded as data to one of the personal units 2), may be such as to provide both functional stimulation, that is stimulation which causes muscle fibres to contract and relax in a predetermined way, or may be the "trophic" stimulation mentioned above, that is stimulation with pulses whose characteristics are chosen such that they effect a long term structural or functional change in the muscle fibres.

In order to treat certain types of muscular disorder, it may be necessary to bring about long term changes in the structure and/or function of the muscle fibre as well as to provide for functional stimulation and it is therefore envisaged that a course of treatment may comprise a mix of trophic stimulation and functional stimulation with more frequent use of trophic stimulation at the early stages of the treatment and or frequent use of functional stimulation towards the end. In some cases it may necessary for the start of treatment to consist wholly of trophic stimulation at the start.

It is envisaged that such a course of treatment comprising data defining sets of pulse series, some of which provide functional stimulation, and some of which provide trophic stimulation may be programmed into the personal unit 2 by the control unit 1 so that the patient may take the personal unit away and use it for treatment at home. The data defining the stimulation to be applied may be updated from time to time by taking the unit 2 back to the unit 1 and down-loading the up-dated information. Preferably, therefore, the personal unit 2 is so programmed as to store in its memory 420 an indication of the characteristics of the current stimulation pattern(s) and a record of the number of times that the patient has applied them so that these items of information may be transmitted via the data link to the control unit 1 and thereby enabled the correct data for the next phase of treatment to be identified and down-loaded to the personal unit 2.

As mentioned above, the control unit 1 has an interface 4 interfacing with a computer such as a personal, desktop or personal computer, preferably of the type which has disc drives or other non-volatile storage so that a database of stimulation pulse data can be stored and specific files retrieved and loaded into the memory 420 of the unit 1 so as to be available for the direct generation of pulses by the pulse generator 430 or for down-loading to the personal units 2. The computer to which the control unit 1 is linked, preferably by a industry-standard parallel or serial link such as the RS232 (serial) or Centronics interface (parallel) may be programmed to accept data files of pulse stimulation data from the control unit 1 and of any other data which can be selected by the operator of the unit via the section 380 and which it would be convenient to store in a mass storage device and retrieve at a later date, for example patient data, treatment details and so forth.

Both the personal unit 2 and the control unit 1 may be provided with a modem for exchanging data with one another or with a remote computer base so as to enable stimulation pulse data and other useful data to be stored and or processed by the remote computer or exchanged between the personal unit 2 and the control 1 when it is not possible to bring them physically together. To assist in achieving this, the personal unit 2 may have a microphone and loudspeaker arranged so that they can be held against the handset of a standard telephone, in which case as with conventional portable modems, these items may be surrounded by soundproofing material to shut out extraneous noise and, instead or as well, the personal units 2 and the control unit 1 may be provided with an internal modem directly connected to a standard telephone jack plug.

It will be apparent from the above that once suitable treatment regimes have been established, the pulse data and other relevant information relating to these may be transferred direct to the personal units 2 from a remote or on-site computer without the intervention of the controller 1.

The overall specification of the facilities of the controller 1 is as follows:

Controls
8 independent amplitude slide controls
1 Rise/Fall time control
Full numeric keypad and parameter selection and display controls.
Power Rechargeable NiCd Batteries or Power Supply.
Frequency : 2-99 pps
Contraction Time : 1-99 sec
Relaxation Time : 0-99 sec
Pulse Width : 20-400 uSec
Rise/Fall Time : 0-5 sec
Pulse Format : sub pulses or extended pulses
Output Format : synchronous or alternate
Built in Programs : 10 user-redefinable (more if necessary).
Built in trophic codes : 10 re-programmable
Interfaces:
1. Optical link for personal stimulator 2
2. Parallel link with research unit 3.
3. External independent trigger for evaluation of functional stimulation.
4. Parallel link with Personal Computer to allow infinite selection of user program files.

The following points should be noted :

(a) As a stand-alone instrument the system controller may be used in Hospitals and Clinics with direct therapeutic application.

(b) A successful treatment regime may be easily down-loaded to a personal unit instrument for continued treatment of patients at home.

(c) When connected to the research unit 3 the instrument's eight outputs are under full control of the unit 3 and its associated computer.

(d) When connected direct to a computer the instrument may have an infinite number of patient specific programs or trophic codes down loaded to it or via its optic link to a personal stimulator 2.

(e) The optical link could be further expanded to interface with a modem to allow remote programming.

The overall specifications of the personal units 2 are as follows:

2 channel portable microcomputer controlled electronic neuromuscular stimulator.
Controls
2 amplitude external
1 Rise/Fall time internal
Power - Rechargeable NiCd Batteries
Frequency : 2-99 pps
Contraction Time : 1-99 sec
Relaxation Time : 0—99 sec
Pulse Width : 20-400 uSec
Rise/Fall Time : 0-5 sec
Pulse Format : sub pulse or extended pulse synchronous or alternate All parameters optically programmable on infra-red link with host machine/system controller. Failure to program or subsequent accidental program loss will trigger an error detection indicator.

Option : trophic code and/or functional code replaceable memory cartridges.

Figure 5:
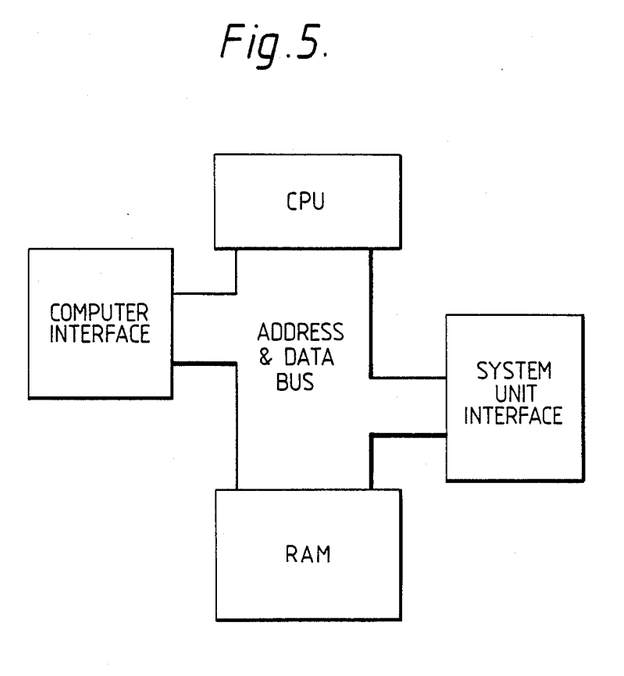
FIG. 5 is a block diagram of the circuitry of the research unit.

The research unit 3 is adapted to be used in association with the system controller 1 to provide an 8 channel sophisticated computer driven neuromuscular stimulation controller for extensive research application; it may have inter alia RS232 and IEEE 488 interfaces for communication with the host computer which is to be used to control it, as well as a suitable e.g. parallel interface for communicating with the system controller 1.

The instrument will be supplied with elaborate software control modules to run on its host computer and will be controlled by it over standard interfaces.

The research unit instrument interfaces directly to the controller 1 and captures full control over its eight stimulation outputs.

Each channel is totally independent and may be controlled in frequency pulse width, contraction time, relaxation time, rise time, fall time and amplitude. Sophisticated envelope waveforms for the stimulation amplitude may be generated graphically on the host computer. Precision timing between stimulation channels may be set-up thus allowing elaborate functional stimulation and gait control experiments.

Alternately the research unit may be used to generate and emulate exceedingly complex trophic code stimulation patterns used in experimental research into the fundamentals of neurophysiology.

Interfaces : RS 232C and IEEE 488 : Parallel interface to system controller 1.

Host Computer : Apple IIe IBM PC

Details of one optical interface between the personal unit 2 and the controller 1 are as follows:

Mode : Infra-red 950 nM

Data Rate : 1200 baud

Data Format : RS 232 format Serial 11 bits even parity

Information Type: Control Codes–single ASCII character Parameter Codes–double ASCII character command plus maximum of eight characters numeric information delimited by carriage return.

Interface operates in half-duplex mode.

A communication protocol for use by this link and for other data transfers between the units may be based on the standard ASCII codes and comprise a series of control codes and parameter codes as follows:

| Control Code | ASCII | Hex |
| --- | --- | --- |
| No operation | NUL | 00 |
| Send Information | SOH | 01 |
| Request Information | ENQ | 05 |
| End of Transmission | EQT | 04 |
| Sound Bell | Bel | 07 |

| PARAMETER | CODE | CHANNEL | BYTES | UNITS |
| --- | --- | --- | --- | --- |
| Frequency | FQ | n | xxx | pps |
| Contraction | CT | n | xxx | sec |
| Relaxation | RL | n | xxx | sec |
| Pulse-Width | PW | n | xxxx | uS |
| Rise-Time | YT | | x | sec |
| Fall-Time | ZT | | x | sec |
| Treatment Time | XT | | xxx | min |
| User time elapsed since last program | UT | | xxxxx | min |
| Date | DT | | xxxxxx | mth, date, year |
| Output Format | AS | | A or S | |
| Pulse Format | MP | | E or S | |
| Serial No. | NO | | xx | |
| Trophic Code | KC | n | k1, k2, xxx | mS |

We claim:

1. A muscle stimulator system for the electrical stimulation of muscles by the application of electrical pulses to the skin overlying the muscle, comprising at least one muscle stimulator apparatus for generating the said electrical pulses, an electrode arrangement to be applied to the skin overlying the muscle and connected to the stimulator apparatus to receive the said electrical pulses and a system controller, wherein the system controller is provided with at least one of (a) means for storing data representative of stimulation treatment regimes; and (b) user operable means for defining a stimulation treatment regime and means for generating therefrom data representative of the stimulation treatment sequence, and wherein the system controller further comprises means for transferring to the stimulator apparatus the data representative of the thus defined characteristics of the stimulation treatment to program the stimulator apparatus with a treatment regime and wherein the system controller and muscle stimulator apparatus are separate units, the muscle stimulator apparatus having receiving means for receiving said data from the system controller, the system controller including at least one receptacle into which the muscle stimulator apparatus is adapted to fit, the transferring means of the system controller and the receiving means of the muscle stimulator apparatus being mutually adapted such that said data can be transferred to the muscle stimulator apparatus when the muscle stimulator apparatus occupies the receptacle and in a manner which does not require electrical connection of the means for transferring to the receiving means, the muscle stimulator apparatus comprises a self-contained unit comprising a meory for storing the stimulation data transferred from the system controller, pulse generating means for generating said stimulation pulses in response to and in accordance with the stored data and a power supply, and is of such a size and shape that it is personally portable by the patient and includes means allowing the stimulator apparatus to be worn by the patient so that it may be carried about by the patient, whereby the stimulator apparatus may be operated to administer the programmed treatment regime remote from the system controller.

2. A muscle stimulator system according to claim 1, wherein the memory in the at least one stimulator apparatus comprises a read/write memory and means are provided for writing to the read/write memory data representative of the electrical pulses supplied to said electrode arrangement as said treatment regime and means are provided for subsequently supplying that data to the system controller; when the stimulator apparatus occupies the receptacle.

3. A muscle stimulator system according to claim 1, wherein said means for storing the data representative of stimulation treatment regimes stores data representative of a series of trophic stimulating pulses and said user operable means comprise means for defining a series of trophic stimulation pulses and said pulse generating means comprise means for generating therefrom a series of trophic stimulation pulses.

4. A muscle stimulator system according to claim 1, wherein said means for storing the data representative of stimulation treatment regimes stores data representative, of a series of functional stimulating pulses and said user operable means comprises means for defining a series of functional stimulating pulses and said pulse generating means comprise means for generating therefrom a series of functional stimulating pulses.

5. A muscle stimulator system according to claim 1 wherein the at least one stimulator apparatus and electrode arrangement are an integral unit, the unit being adapted to be mounted, in use, on the skin overlying the muscle to be stimulated.

6. A muscle stimulator system according to claim 1 wherein the means for transferring the said data between the system controller and the at least one muscle stimulator apparatus comprises an infra-red link.

7. A muscle stimulator system according to claim 1 further comprising a muscle stimulation control device including means adapted to be connected to the system controller and to a computer whereby the system controller may be controlled by an external computer and data may be transferred from the system controller to the computer.

8. A muscle stimulator system according to claim 1 wherein the system controller further includes a muscle stimulator.

9. A muscle stimulator system according to claim 1 wherein the system controller and stimulator apparatus are adapted to transfer the data representing the stimulation treatment sequence from the system controller to the at least one stimulator apparatus in the following form:

| Control Code | ASCII | Hex |
|---|---|---|
| No operation | NUL | 00 |
| Send Information | SOH | 01 |
| Request Information | ENQ | 05 |
| End of Transmission | EQT | 04 |
| Sound Bell | Bel | 07 |

| PARAMETER | CODE | CHANNEL | BYTES | UNITS |
|---|---|---|---|---|
| Frequency | FQ | n | xxx | pps |
| Contraction | CT | n | xxx | sec |
| Relaxation | RL | n | xxx | sec |
| Pulse-Width | PW | n | xxxx | uS |
| Rise-Time | YT | | x | sec |
| Fall-Time | zT | | x | sec |
| Treatment Time | XT | | xxx | min |
| User time elapsed since last program | UT | | xxxxx | min |
| Date | DT | | xxxxxx | mth, date, year |
| Output Format | AS | | A or S | |
| Pulse Format | MP | | E or S | |
| Serial No. | NO | | xx | |
| Trophic Code | KC | n | k1, k2, xxx | ms. |

10. A muscle stimulator system according to claim 1 wherein the at least one stimulator apparatus includes a radio receiver and the system controller includes a radio transmitter, the at least one stimulator apparatus being responsive to radio signals from the system controller to output the programmed treatment regime.

11. A muscle stimulating system for the electrical stimulation of muscles by the application of electrical pulses to the skin overlying the muscle comprising a stimulator for generating from data representative of a stimulation treatment sequence the electrical pulses and supplying them to an output, an electrode which, in use, is applied to the skin overlying the muscle and connected to the output of the stimulator to receive the electrical pulses, and one or more electronic programmable control modules which are preprogrammed with the data representative of the treatment sequence to be applied to a muscle and which, in use, communicate with and control the stimulator to supply the generated train of pulses to the electrode the stimulator including processing means for reading the preprogrammed data from the module and generating said pulses in accordance with said data, the stimulator and module being of such a size and shape that they are personally portable by the patient when connected together for communication and including means allowing the stimulator and module to be worn by the patient so that it may be carried about by the patient.

12. A muscle stimulating system according to claim 11 further including a system controller including programming means for programming the control modules with the data representative of the stimulation treatment sequence to be applied to the muscle, the programming means including transferring means for transferring data representative of said stimulation treatment sequence to said control modules.

13. A muscle stimulator system according to claim 12 wherein the control module further includes read/write memory means to store a record of the pulses supplied to the muscle and means for subsequently transferring the record from the read/write memory means to the system controller.

* * * * *